(12) United States Patent
Wang

(10) Patent No.: US 7,885,444 B2
(45) Date of Patent: *Feb. 8, 2011

(54) METHOD FOR DETERMINING A RESPONSE OF EACH PROBE ZONE ON A TEST STRIP

(75) Inventor: Kuo-Jeng Wang, Kaohsiung (TW)

(73) Assignee: Transpacific Systems, LLC, Wilmington, DE (US)

(*) Notice: Subject to any disclaimer, the term of this patent is extended or adjusted under 35 U.S.C. 154(b) by 0 days.

This patent is subject to a terminal disclaimer.

(21) Appl. No.: 11/742,976

(22) Filed: May 1, 2007

(65) Prior Publication Data

US 2007/0223781 A1 Sep. 27, 2007

Related U.S. Application Data

(62) Division of application No. 10/390,602, filed on Mar. 19, 2003, now abandoned.

(30) Foreign Application Priority Data

Dec. 27, 2002 (TW) .............................. 91137722 A

(51) Int. Cl.
*G06K 9/00* (2006.01)
(52) U.S. Cl. .................................... 382/128; 382/196
(58) Field of Classification Search .................. 435/4, 435/970; 422/87; 382/196, 128; 348/812
See application file for complete search history.

(56) References Cited

U.S. PATENT DOCUMENTS

| 3,745,527 A | 7/1973 | Yoshimura et al. |
| 4,044,227 A | 8/1977 | Holm et al. |
| 4,806,311 A | 2/1989 | Greenquist |
| 5,075,078 A | 12/1991 | Osikowicz et al. |
| 5,087,556 A | 2/1992 | Ertinghausen |
| 5,107,422 A | 4/1992 | Kamentsky et al. |

(Continued)

FOREIGN PATENT DOCUMENTS

JP 2000060803 2/2000

OTHER PUBLICATIONS

Stolowitz Ford Cowger LLP, Listing of Related Cases, Jun. 15, 2010.

(Continued)

*Primary Examiner*—Matthew C Bella
*Assistant Examiner*—Dennis Rosario
(74) *Attorney, Agent, or Firm*—Stolowitz Ford Cowger LLP

(57) ABSTRACT

A method for determining a response of each probe zone on a test strip is provided. The present invention selects an average pixel value of each section of reference white respectively adjacent to the image of a target line to serve as a reference for determining a color response of the target line. When the color response is not less than a predetermined value, representing the target line has a positive response in response to a specific component of a tested solution tested by the test strip, and the specific component is present in the tested solution. The content of the specific component is proportional to the color response. When the color response is less than a predetermined value, representing the target line has a negative response in response to the specific component of the tested solution, and the specific component is absent in the tested solution.

26 Claims, 3 Drawing Sheets

U.S. PATENT DOCUMENTS

| | | | |
|---|---|---|---|
| 5,145,789 A | 9/1992 | Corti et al. | |
| 5,200,317 A | 4/1993 | Georgevich | |
| 5,229,073 A | 7/1993 | Luo et al. | |
| 5,234,813 A | 8/1993 | McGeehan et al. | |
| 5,238,652 A | 8/1993 | Sun et al. | |
| 5,323,473 A | 6/1994 | Lau | |
| 5,394,342 A | 2/1995 | Poon | |
| 5,408,535 A * | 4/1995 | Howard et al. | 382/128 |
| 5,415,994 A | 5/1995 | Imrich et al. | |
| 5,500,350 A | 3/1996 | Baker et al. | |
| 5,602,040 A | 2/1997 | May et al. | |
| 5,656,503 A | 8/1997 | May et al. | |
| 5,714,341 A | 2/1998 | Thieme et al. | |
| 5,753,519 A | 5/1998 | Durst et al. | |
| 5,761,070 A * | 6/1998 | Conners et al. | 700/223 |
| 5,798,273 A | 8/1998 | Shuler et al. | |
| 5,804,452 A | 9/1998 | Pronovost et al. | |
| 5,817,526 A * | 10/1998 | Kinoshita et al. | 436/526 |
| 5,843,691 A | 12/1998 | Douglas et al. | |
| 5,916,815 A | 6/1999 | Lappe | |
| 5,969,371 A | 10/1999 | Andersen et al. | |
| 6,046,058 A | 4/2000 | Sun | |
| 6,095,661 A * | 8/2000 | Lebens et al. | 362/184 |
| 6,194,220 B1 | 2/2001 | Malick et al. | |
| 6,194,221 B1 | 2/2001 | Rehg et al. | |
| 6,248,596 B1 | 6/2001 | Durst et al. | |
| 6,388,788 B1 * | 5/2002 | Harris et al. | 359/196 |
| 6,475,805 B1 | 11/2002 | Charm et al. | |
| 6,492,127 B2 | 12/2002 | Goodell et al. | |
| 6,528,325 B1 | 3/2003 | Hubscher et al. | |
| 6,627,459 B1 | 9/2003 | Tung et al. | |
| 6,663,831 B2 | 12/2003 | Konecke | |
| 6,689,618 B1 | 2/2004 | Chen | |
| 6,767,714 B2 | 7/2004 | Nazareth et al. | |
| 7,070,920 B2 * | 7/2006 | Spivey et al. | 435/4 |
| 7,097,103 B2 | 8/2006 | Tseng | |
| 7,197,169 B2 | 3/2007 | Wang | |
| 2002/0001852 A1 | 1/2002 | Mendel-Hartvig et al. | |
| 2002/0081233 A1 | 6/2002 | Lappe et al. | |
| 2003/0040128 A1 | 2/2003 | Meador et al. | |
| 2004/0095360 A1 | 5/2004 | Tseng et al. | |
| 2004/0131238 A1 | 7/2004 | Wang | |
| 2004/0162690 A1 * | 8/2004 | Lee | 702/105 |
| 2007/0196862 A1 | 8/2007 | Wang | |

OTHER PUBLICATIONS

Prosecution History for U.S. Appl. No. 10/334,798, filed Jan. 2, 2003.

Prosecution History for U.S. Appl. No. 11/674,593, filed Feb. 13, 2007.

\* cited by examiner

METHOD FOR DETERMINING A RESPONSE OF EACH PROBE ZONE ON A TEST STRIP

CROSS-REFERENCE TO RELATED APPLICATIONS

This is a Divisional Patent Application of U.S. patent application Ser. No. 10/390,602, filed Mar. 19, 2003, now abandoned which claims the benefit of foreign priority under 35 USC §119(a) to Taiwan, R.O.C Application Serial No. 091137722, filed Dec. 27, 2002.

BACKGROUND OF THE INVENTION

1. Field of the Invention

The present invention relates to a method for determining a response of each probe zone on a test strip, and more particularly to a method for determining a response of each probe zone on a test strip via an image capturing technology.

2. Description of the Prior Art

Over the past decade, there has been an increased need and demand for analysis of various biological specimens, for purposes ranging from pregnancy testing to drug analysis. Considerable time and effort has been expended by way of devising systems and analytic techniques to ensure reliable testing and accurate results.

Moreover, with increasing rise in the use of abuse-type drugs, the need for detecting and identifying those drugs and their metabolites is becoming more important. With this need, many more tests are required to monitor the use of abuse-type drugs.

Thin layer chromatography (TLC) screening procedures for detecting drugs in urine require the careful preparation of a test specimen and then a skillful application of that test specimen to a plate placed into a developing chamber. Once the plate is removed from the chamber and dried, it is sprayed with visualization reagents. Location and color of spots are compared with those of known standards. Qualitative judgements are made as to the presence of various drugs in the unknown sample. The procedure is tedious, time consuming and requires skilled personnel to interpret the results.

The EMIT (Enzyme Multiplied Immuno-chemical Test) procedure is a semi-quantitative immuno-assay for drugs of abuse in biological fluids. The laboratory test requires trained technicians to perform and the equipment necessarily costs several thousands of dollars.

The RIA (Radio-Immuno-Assay) procedure is a sensitive and quantitative laboratory procedure for detecting drugs of abuse. The various immunochemicals are labeled with radioactive compounds and require special care in their use and disposal. A license is required from the government to use this laboratory procedure because of the presence of radioactive materials. The GLC (Gas-Liquid Chromatography) procedure can provide the highest degree of accuracy in drug analysis. However, the necessary equipment is expensive and the procedure is complicated. Consequently, highly trained personnel are required for its use.

Each of these well-known procedures requires skilled technicians and relatively sophisticated equipment. Consequently, the testing procedure is necessarily expensive.

However, the increase of drug abuse has increased a need for new methods of analyzing drug residues in physiological fluid. A drug abuse test paper for testing the presence or absence of drugs in a fluid specimen collected from a test subject is developed. The drug abuse test paper is prepared in accordance with unique procedure whereby pH insensitivity and color change sensitivities to tested fluids are obtained. The color change of the drug abuse test paper sensitive to one specific substance present in the fluid specimen collected from the test subject applied on the drug abuse test paper is simply verified by visual judgement. This abuse-type drug testing is rapid and convenient. However, it is not convincing for concluding the test subject has used abuse-type drugs.

Accordingly, it is an intention to provide means capable of detecting and identifying the presence or absence of drugs of abuse in a fluid specimen, which can overcome the problems of the conventional methods.

SUMMARY OF THE INVENTION

It is one objective of the present invention to provide a method for determining a response of each probe zone on a test strip, which quantifies a color response of each probe zone on the test strip in response to a tested solution so as to monitor specific components present in the tested solution and the contents thereof.

It is another objective of the present invention to provide a method for determining a response of each probe zone on a test strip, which selects an average pixel value of each section of pixels corresponding to an image of a light color base of the test strip respectively adjacent to an image of a target line on the test strip to serve as a reference for quantifying a color response of the target line. As a consequence, the present method can effectively determine whether the target line has a positive response or negative response in response to a tested solution tested by the test strip, and furthermore effectively monitor specific components present in the tested solution.

It is still another objective of the present invention to provide a method for determining a response of each probe zone on a test strip, which can be utilized to detect drugs of abuse present in a tested solution.

It is yet another objective of the present invention to provide a method for determining a response of each probe zone on a test strip, which is quick and convenient to use by non-sophisticated personnel in non-laboratory settings, and performs assays for multiple drugs of abuse simultaneously.

It is a further objective of the present invention to provide a method for determining a response of each probe zone on a test strip, which associates with an image capturing/processing technology to analyze drug residues in physiological fluid to attain the purposes of accuracy, rapid and cost effective in drug abuse detection technology.

In order to achieve the above objectives of this invention, the present invention provides a method for determining a response for each probe zone on a test strip. The present method includes providing a test strip having a light color base and a color pattern displayed thereon. The color pattern occurs in response to a tested solution contacting with the test strip and including a plurality of target lines and one control line displayed in sequence from a bottom portion of the test strip to a top portion thereof. The site of each target line represents a probe zone of the test strip and a color shade of each target line is inversely proportional to a content of a specific component of the tested solution. The control line displays a color response in response to the tested solution. Capturing a whole image of the test strip, and then selecting at least one scan line from the whole image. The scan line is perpendicular to the image of the target lines and the control line. A diagram of pixel value versus pixel position for the target lines and the control line in accordance with the scan line is thus established. Determining a color response R of each target line from the diagram and in accordance with a formula (I):

$$R = \{(T-C)/(A-C)\} \times 100\% \qquad (I),$$

wherein T represents an average pixel value of a section of pixels corresponding to the image of the target line, C represents an average pixel value of a section of pixels corresponding to the image of the control line, and A represents an average pixel value of a first section of pixels and a second section of pixels corresponding to the images of the light color base respectively adjacent to the image of the target line. When the color response R is not less than a predetermined value, defining the target line has a positive response in response to a specific component of the tested solution, representing the specific component is present in the tested solution and a content of the specific component is proportional to the color response R. When the color response R is less than the predetermined value, defining the target line has a negative response in response to the specific component of the tested solution, representing the specific component is absent in the tested solution.

The present invention associates with an image capturing/processing technology to obtain a whole image of a test strip including a plurality of target lines and one control line. Selecting an average pixel value of each section of reference white respectively adjacent to an image of a target line to serve as a reference for determining a color response of the target line. The present invention can effectively determine color responses of the target lines on the test strip, and furthermore effectively monitor specific components present in a tested solution tested by the test strip.

BRIEF DESCRIPTION OF THE DRAWINGS

The objectives and features of the present invention as well as advantages thereof will become apparent from the following detailed description, considered in conjunction with the accompanying drawings.

DESCRIPTION OF THE PREFERRED EMBODIMENT

From a view of broad application, the present invention provides a method for determining a response of each probe zone on a test strip after testing a sample solution. The present invention associates with an image capturing/processing technology to detect respective responses of the probe zones on the test strip so as to qualitatively and quantitatively identify specific substances in the sample solution. More specifically, the present invention utilizes the image capturing technology to capture the whole image of a test strip having a color pattern displayed thereon. The color pattern includes a plurality of target lines each of which representing a probe zone of the test strip having a color change in response to a specific substance in the sample solution. In accordance with the image of the color pattern of the test strip, the response of each probe zone of the test strip in response to the sample solution can be determined so as to detect the presence or absence of the specific substance related to in the sample solution. The present method is suitable to be used as a drug abuse detection technology. That is, the present method can be used to detect and quantify a color response of each probe zone on a drug abuse test strip after testing a physiological fluid, such as urine, blood, sweat and saliva, collected from a subject, instead of visual judgment of the color responses of the probe zones on the drug abuse test strip.

Figure 1A:
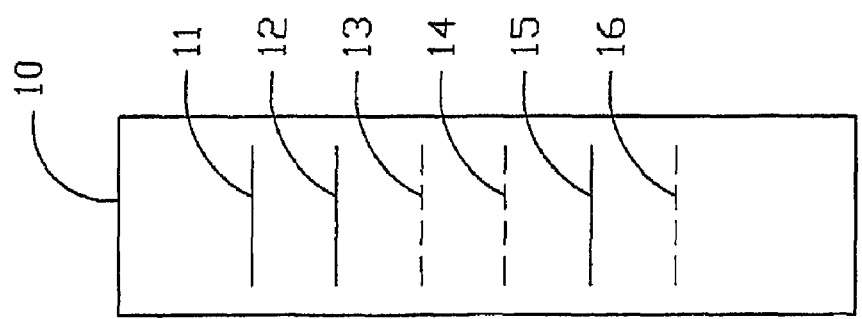
FIG. 1A to FIG. 1D shows schematic top views of a drug abuse test strip under various testing situations of the present invention.

The present method will be described in detail with a drug abuse test strip as an example in the following. However, before detailed description of the present method, an introduction of various color patterns occurring on one drug abuse test strip under various testing situations is provided herein. Firstly, referring to FIG. 1A, which is a schematic top view of a drug abuse test strip 10 prior to testing a sample fluid collected from a subject. The drug abuse test strip 10 is blank and no color pattern displayed thereon prior to testing the sample fluid. The dotted lines 11 through 16 respectively represent a probe zone of the drug abuse test strip 10. The top probe zone of the drug abuse test strip 10 corresponding to the site of dotted line 11 displays color change in response to the sample fluid, which is used to indicate whether the amount of the sample fluid is sufficient to move through all probe zones of the drug abuse test strip 10 by capillary action. The color line displayed on the top probe zone is called control line. The other probe zones of the drug abuse test strip 10 corresponding to the sites of dotted lines 12 through 16 respectively display color change in response to a respective drug of abuse presenting in the sample fluid. The color lines displayed on these probe zones are called target lines. It should be noted the drug abuse test strip used in the present invention is not limited to the kind of the drug abuse test strip 10 of FIG. 1A.

Figure 1B:
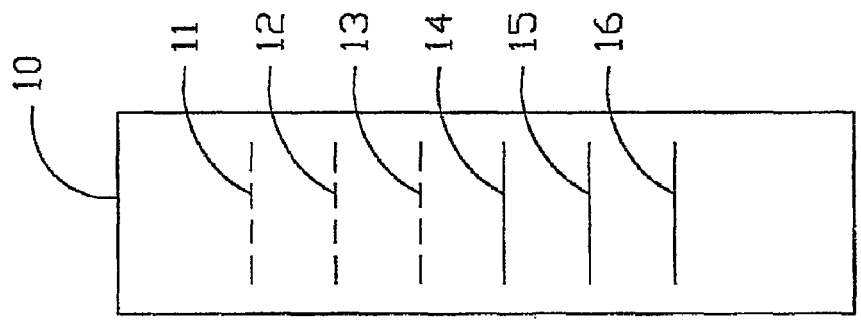
Figure 1C:
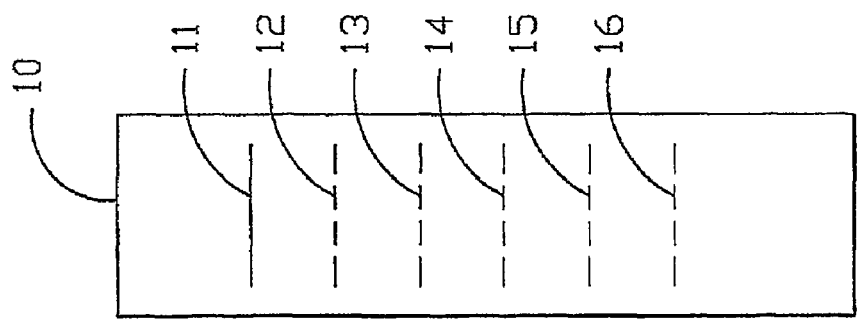
Figure 1D:
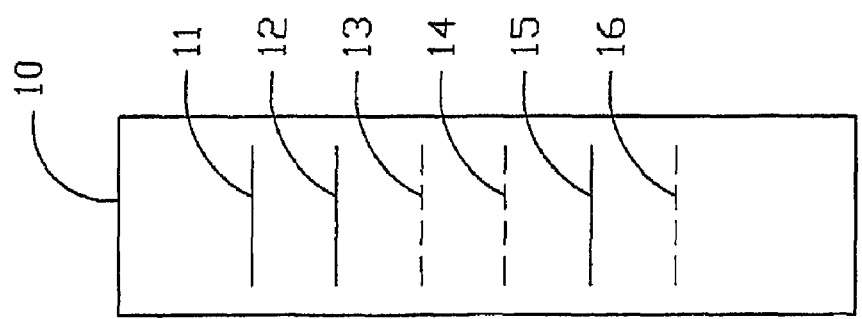

Referring to FIG. 1B, which shows a color pattern of the drug abuse test strip 10 having no color change occurring in the top probe zone represented by the dotted line 11, which is under a testing situation that the amount of the sample fluid is not sufficient to assure the sample fluid moves through all probe zones of the drug abuse test strip 10. Therefore, in accordance with the color pattern consisting of solid lines 14 through 16 shown in FIG. 1B, the drugs of abuse presenting in the sample fluid cannot completely detected and identified. Referring to FIG. 1C, which shows a color pattern of the drug abuse test strip 10 having only one color line 11 displayed in the top probe zone of the drug abuse test strip 10. It means the top probe zone has a positive response in response to the sample fluid. The amount of the sample fluid is sufficient to pass through all probe zones on the drug abuse test strip 10. All other probe zones represented by the dotted lines 12 through 16 have positive responses to the sample fluid, and all drugs of abuse corresponding to these probe zones present in the sample fluid. Referring to FIG. 1D, which shows a color pattern of the drug abuse test strip having color lines 11, 12 and 15 displayed in the top probe zone and some other probe zones of the drug abuse test strip 10, which means the top probe zone 11 has a positive response to the sample fluid, indicating the amount of the sample fluid is sufficient, and the probe zones represented by the color lines 12 and 15 have a negative response to the sample fluid, indicating that the absence of the drugs of abuse corresponding to these two probe zones in the sample fluid. On the contrary, the probe zones represented by the dotted lines 13, 14 and 16 have a positive response to the sample fluid, indicating that the presence of the drugs of abuse corresponding to these three probe zones in the sample fluid.

The top probe zone on the drug abuse test strip 10 has a positive response in response to the sample fluid, a color response occurs. That is, the control line 11 would display thereon. One of the other probe zones on the drug abuse test strip 10 has a positive response in response to a specific substance of the sample fluid, there is no color response occurs on the probe zone. It means the specific substance is present in the sample fluid, and there is a highly content of the specific substance in the sample fluid. However, one of the other probe zones on the drug abuse test strip 10 has a negative response in response to a specific substance of the sample fluid, a color response, i.e. target line, is displayed on the probe zone. The color shade of the target line can be used to monitor the content of the specific substance or even represents absence of the specific substance in the sample fluid. The color shade of each of the target lines 12 to 16 is inversely proportional to the content of a specific substance to be detected in the sample fluid. The higher the content of the specific substance is, the lighter the color shade of the target line is. The present method can quantify a color response of each probe zone on a test strip so as to effectively monitor specific substances present in a sample fluid tested by the test strip and determine contents thereof.

The present invention will be described and explained in detail in accordance with preferred embodiments with reference to accompanying drawings.

Figure 2:
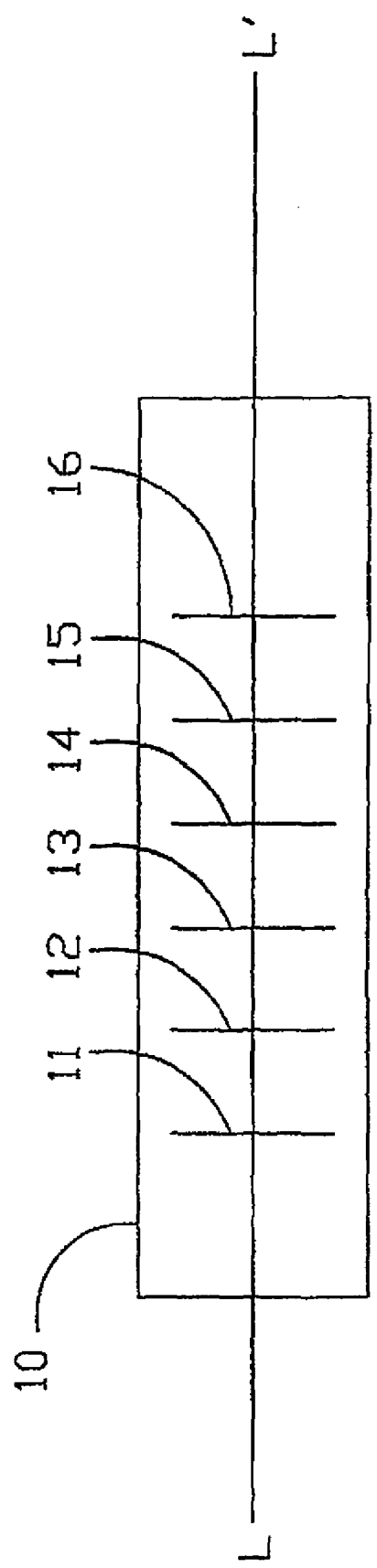
FIG. 2 is a schematic top view of a drug abuse test strip after testing a sample fluid of the present invention.
Figure 3:
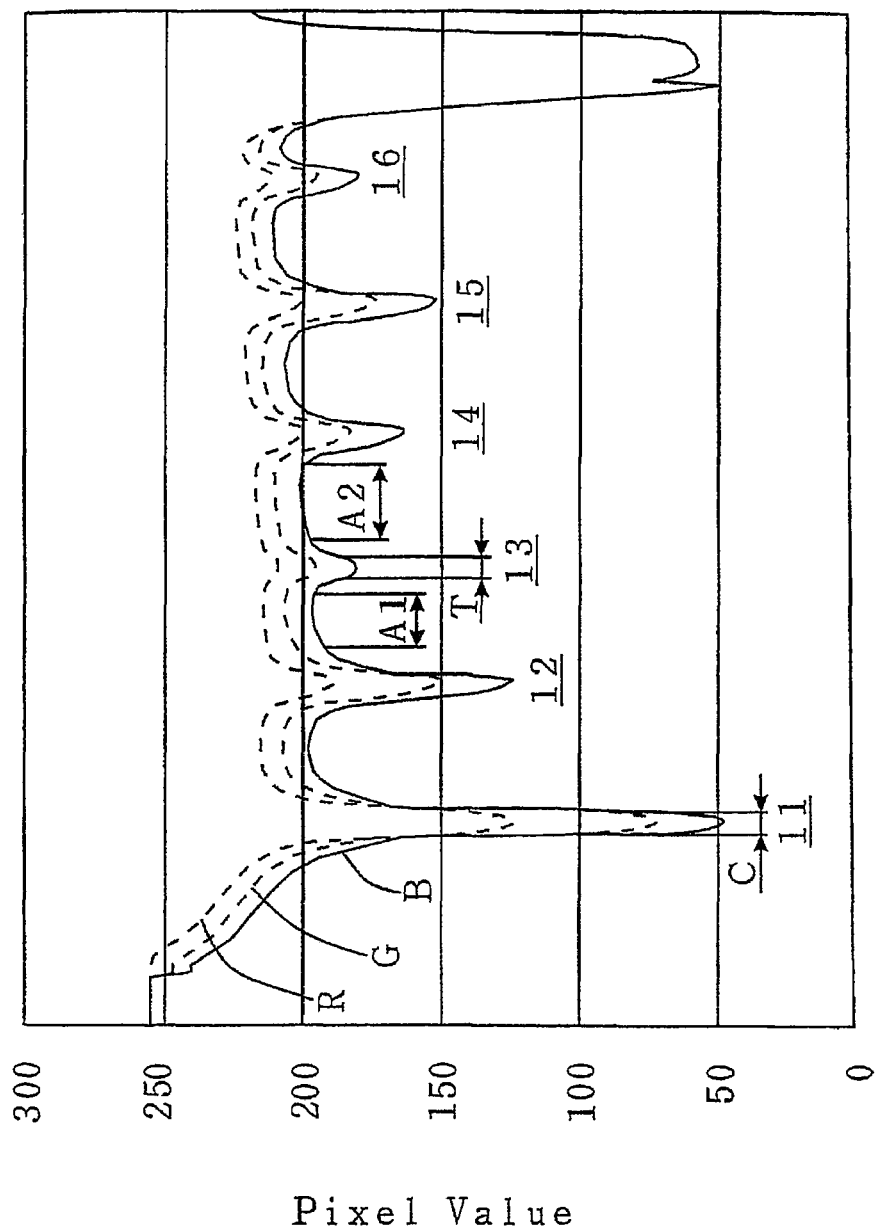
FIG. 3 is a diagram of pixel value versus pixel position established in accordance with one scan line selected from a whole image captured from the drug abuse test strip of FIG. 2.

In accordance with a first preferred embodiment, referring to FIG. 2, the drug abuse test strip 10 having a light color base, such as white base, and a color pattern displayed thereon, is provided. The color pattern occurs in response to a tested solution contacting with the drug abuse test strip 10. The color pattern includes one control line 11 and a plurality of target lines 12 to 16 in sequence from a top portion of the drug abuse test strip 10 to a bottom portion thereof. The control line 11 and target lines 12 to 16 have the same color, but different color shades. The sites of the control line 11 and the target lines 12 to 16 respectively represent a probe zone on the drug abuse test strip 10. The color line 11 displayed on the top probe zone of the drug abuse test strip 10 represents the top probe zone has a positive response in response to the tested solution. However, one of the other probe zones on the drug abuse test strip 10 has a positive response in response to the tested solution, a color response, i.e. a target line, would not display on the probe zone, or only a target line having a light color shade displays on the probe zone. That means a specific component to be detected by the probe zone is present in the tested solution. On the contrary, one of the other probe zone has a negative response in response to the tested solution, a dark color response, i.e. a target line, would display on the probe zone. That means a specific component to be detected by the probe zone is absent in the tested solution. In the present invention, the color shade of the target line is inversely proportional to the content of the specific component in the tested solution. The whole image of the drug abuse test strip 10 is then captured by an image capturing device, such as a scanner associated with a charge-coupled device (CCD). Referring to FIG. 2, selecting at least one scan line L-L' from the whole image. The scan line L-L' is perpendicular to the image of the control line 11 and target lines 12 through 16. A diagram of pixel value versus pixel position for the whole image of the drug abuse test strip 10 is established in accordance with the scan line L-L', as shown in FIG. 3. The diagram of FIG. 3 shows three curves respectively representing the relationship of pixel value and pixel position for red (R), green (G), blue (B) channels of the charge-coupled device, which are called red pixel curve, green pixel curve and blue pixel curve herein. The R, G, B channels are disposed on the charge-coupled device in parallel, and each of the R, G, B channels including a plurality of sensor cells, and each sensor cell corresponding to a pixel position. Alternately, the present invention can utilize a charge-coupied device with a single channel, such as a charge-coupled device with a red channel, a charge-coupled device with a green channel or a charge-coupled device with a blue channel, to capture the whole image of the drug abuse test strip 10.

As shown in FIG. 3, the levels of the pixels corresponding to the image of the light color base of the drug abuse test strip 10 adjacent to the image of each of target lines 12 to 16 have a trend of gradually increasing. It would have a difficulty to judge whether one of the target lines 12 to 16 represents a positive response or negative response in response to the tested solution when selecting an average pixel value of a section of pixels or only a single pixel corresponding to the image of the light color base of the drug abuse test strip 10 adjacent to the target line as a reference to determine the color response of the target line in response to the tested solution. A color response R of each of the target lines 12 to 16 of the drug abuse test strip 10 is determined based on one of the red pixel curve, the green pixel curve and the blue pixel curve selected from the diagram of FIG. 3 and in accordance with a formula (I) of R={(T−C)/(A−C)}×100% in the first preferred embodiment of the present invention. For example, the color response R of the target line 13 can be determined from the blue pixel curve and based on the formula (I) of R={(T−C)/(A−C)}×100%, wherein T represents an average pixel value of a section of pixels corresponding to the image of the target line 13, C represents an average pixel value of a section of pixels corresponding to the image of the control line 11, and A represents an average pixel value of a first section $A_1$ of pixels and a second section $A_2$ of pixels corresponding to the images of the light color base respectively adjacent to the image of the target line 13. When the color response R is not less than a predetermined value, defining the target line 13 has a positive response in response to a specific component of the tested solution. That means the specific component is present in the tested solution. A content of the specific component is proportional to the color response R. When the color response R is less than the predetermined value, defining the target line 13 has a negative response in response to the specific component of the tested solution. That means the specific component is absent in the tested solution.

In a second preferred embodiment of the present invention, selecting one of the red pixel curve, the green pixel curve and the blue pixel curve from the diagram of FIG. 3, and determining a color response R of one of the target lines 12 to 16 in accordance with the selected curve and based on the formula (I) of R={(T−C)/(A−C)}×100%. Then, obtaining an average color response of the target line in accordance with the color responses Rs respectively determined from the red pixel curve, the green pixel curve and the blue pixel curve. When the average color response is not less than a predetermined value, defining the target line has a positive response in response to a specific component of the tested solution. That means the specific component is present in the tested solution. A content of the specific component is proportional to the average color response. When the average color response is less than the predetermined value, defining the target line has a negative response in response to the specific component of the tested solution. That means the specific component is absent in the tested solution.

In a third preferred embodiment of the present invention, selecting at least one scan line from the whole image of the drug abuse test strip 10, the scan line is perpendicular to the image of the control line 11 and the target lines 12 to 16. A diagram of pixel value versus pixel position for the control line 11 and the target lines 12 to 16 is established in accordance with the scan line. Then, a color response R of one of the target lines 12 to 16 is determined in accordance with the diagram and based on the formula (I) of R={(T−C/A−C)}×100%, wherein T represents an average pixel value of a section of pixels corresponding to the image of the target line, C represents an average pixel value of a section of pixels corresponding to the image of the control line 11, and A represents an average pixel value of a first section of pixels and a second section of pixels corresponding to the images of the light color base of the drug abuse test strip 10 respectively adjacent to the image of the target line. When the color response R is not less than a predetermined value, defining the target line has a positive response in response to a specific component of the tested solution. That means the specific component is present in the tested solution. A content of the specific component is proportional to the color response R. When the color response R is less than the predetermined value, defining the target line has a negative response in response to the specific component of the tested solution. That means the specific component is absent in the tested solution.

The present invention selects an average pixel value of each section of pixels corresponding to the image of the light color base of the drug abuse test strip 10 respectively adjacent to the image of one of the target lines to serve as a reference for determining a color response of the target line. Thereby, quantitatively judging whether the target line has a positive response or negative response in response to the tested solution. Thus, the present invention can effectively monitor the strength of the color response of each of the target lines in response to the tested solution.

The present method can be automatically performed by an application installed in a computer associated with an image capturing device. The present method is suitable to be used as means to accurately and rapidly detect or identify the presence or absence of drugs of abuse in the sample fluid. And, the present method does not need an expensive equipment and a sophisticated personnel to perform. Thus, the present invention provides an extremely important advance in the drug abuse detection technology. Thousands of tests will no longer have to be conducted using the more sophisticated TLC, EMIT, RIA and GLC procedures.

The embodiments are only used to illustrate the present invention, not intended to limit the scope thereof. Many modifications of the embodiments can be made without departing from the spirit of the present invention.

What is claimed is:

1. A method, comprising:
   capturing an image of at least a portion of a testing device including at least one probe zone, wherein the captured image comprises a test line occurring in the at least one probe zone in response to a tested solution contacting the testing device;
   scanning along a scan line of the image with a scanning system comprising two or more color channels to determine a plurality of color responses from the captured image, wherein the plurality of color responses comprise first image data captured by a first of the two or more color channels using a first frequency of light, and second image data captured by a second of the two or more color channels using a second frequency of light, wherein the first frequency is different than the second frequency, and wherein the scan line passes through the at least one probe zone; and
   determining whether a component of the tested solution is present for the at least one probe zone based, at least in part, on an average of two or more of the plurality of color responses, wherein the two or more of the plurality of color responses are determined from a single scan along the scan line.

2. The method of claim 1, wherein the tested solution comprises a biological specimen.

3. The method of claim 2, wherein the biological specimen comprises blood, urine, sweat, saliva, or combinations thereof.

4. The method of claim 1, wherein the scan line is scanned by the two or more color channels of a charge-coupled device (CCD) to determine the plurality of color responses.

5. The method of claim 4, wherein the color channels are located on the CCD in parallel.

6. The method of claim 1, further comprising determining the plurality of color responses based, at least in part, on average pixel values captured from the test line for each frequency of light.

7. The method of claim 1, wherein the plurality of color responses are associated with red, green, and blue color channels.

8. The method of claim 1, wherein at least one of the plurality of color responses is calculated, at least in part, from:
   a first average pixel value of a section of pixels of the scan line corresponding to the test line;
   a second average pixel value of a section of pixels of the scan line corresponding to a control line, wherein the control line indicates a sufficient amount of the tested solution contacted the testing device; and
   a third average pixel value of a first section of pixels of the scan line and a second section of pixels of the scan line respectively adjacent to the test line.

9. The method of claim 8, wherein the at least one of the plurality of color responses is determined, at least in part, according to the formula $(T-C)/(A-C)$, wherein T corresponds to the first average pixel value, wherein C corresponds to the second average pixel value, and wherein A corresponds to the third average pixel value.

10. The method of claim 1, wherein the scan line of the image is oriented perpendicular to the at least one probe zone.

11. The method of claim 1, wherein the testing device further comprises a control line and a color base, wherein the color base is located adjacent to the test line, wherein the presence of the component of the tested solution is further based on the formula $R=(T-C)/(A-C)$, wherein R corresponds to one of the plurality of color responses, wherein T corresponds to a first average pixel value associated with the test line, wherein C corresponds to a second average pixel value associated with the control line, and wherein A corresponds to a third average pixel value associated with the color base.

12. The method of claim 1, wherein the testing device further comprises a control line and a color base adjacent to the at least one probe zone, and wherein the presence of the component of the tested solution for the at least one probe zone is further determined based on an average of the plurality of color responses determined from pixel values associated with the at least one probe zone, the control line, and the color base.

13. An apparatus, comprising:
   means for capturing an image of at least a portion of a testing device having a probe zone, a control line, and at least one base color adjacent the probe zone, wherein a test line appears in the probe zone in response to a tested solution contacting the testing device;
   means for scanning the testing device along a scan line of the image to determine a plurality of color responses for the probe zone, wherein the scan line passes through the test line, the control line, and the probe zone, wherein the plurality of color responses are determined from scanned image data obtained from a single scan of the testing device, and wherein the scanned image data is obtained using a scanning device having a separate color channel for the plurality of color responses; and means for determining whether a component of the tested solution is present for the probe zone calculated, at least in part, from an average of the plurality of color responses determined from pixel values associated with the probe zone, the control line, and the at least one base color.

14. The apparatus of claim 13, wherein the plurality of color responses are determined from the scanned image data associated with the separate color channel according to a different respective frequency of light.

15. The apparatus of claim 13, wherein the means for scanning comprises means for scanning a plurality of probe zones from the single scan of the testing device, and wherein the plurality of probe zones determine whether a different component of the tested solution is present.

16. An apparatus, comprising:

means for capturing an image of at least a portion of a testing device comprising a probe zone and a control line, wherein a test line appears in the probe zone in response to a tested solution contacting the testing device;

means for scanning the testing device to determine a plurality of color responses for the probe zone, wherein the plurality of color responses are determined from scanned image data obtained from a single scan of the testing device, wherein the scanned image data is obtained using a scanning device comprising a separate color channel for each of the plurality of color responses, wherein a first scanned image data is captured by a first color channel using a first frequency of light, wherein a second scanned image data is captured by a second color channel using a second frequency of light, and wherein the first frequency is different than the second frequency; and means for determining whether a component of the tested solution is present for the probe zone calculated, at least in part, on an average of two or more of the plurality of color responses.

17. The apparatus of claim 16, wherein the testing device further comprises at least one color base adjacent the probe zone, and wherein determining whether the component of the tested solution is present for the particular probe zone is further calculated from an average of the plurality of color responses determined from pixel values associated with the probe zone, the control line, and the at least one color base.

18. A method, comprising:

capturing an image of at least a portion of a testing device comprising a control line and a plurality of probe zones, wherein a test line passes through at least one or more of the plurality of probe zones in response to a tested solution contacting the testing device;

scanning along a scan line of the image to determine a color response for the one or more probe zones, wherein separate color responses are calculated for a red color channel, a green color channel, and a blue color channel of a scanner used to scan the image, wherein the scan line passes through the test line, the control line, and the one or more probe zones, and wherein the scan line is oriented perpendicular to the test line; and determining whether a component of the tested solution is separately present for the one or more probe zones based, in part, on an average of the separate color responses.

19. The method of claim 18, wherein the testing device further comprises a color base located adjacent to the test line, wherein the presence of the component of the tested solution is further based on the formula $R=(T-C)/(A-C)$, wherein R corresponds to the color response, wherein T corresponds to a first average pixel value associated with the test line, wherein C corresponds to a second average pixel value associated with the control line, and wherein A corresponds to a third average pixel value associated with the color base.

20. The method of claim 18, wherein the separate color responses are determined from a single scan of the image.

21. The method of claim 18, wherein the scan line is scanned by a scanning device comprising the red, green, and blue color channels.

22. The method of claim 18, wherein the testing device comprises a drug test strip.

23. The method of claim 18, wherein each of the plurality of probe zones determines whether a different component of the tested solution is present.

24. The method of claim 23, wherein each of the plurality of probe zones is configured to display the test line in response to the tested solution contacting the testing device.

25. The method of claim 18, further comprising establishing a diagram of pixel value versus pixel position in accordance with the scan line, wherein at least one of the plurality of color responses is determined based, at least in part, on the diagram of pixel value versus pixel position.

26. The method of claim 18, wherein the testing device further comprises a color base located adjacent to the test line, and wherein the separate color responses are determined from pixel values associated with at least one of the plurality of probe zones, the control line and the color base.

* * * * *